United States Patent
Piper

(10) Patent No.: US 12,236,059 B2
(45) Date of Patent: *Feb. 25, 2025

(54) SYSTEMS AND METHOD FOR ALGORITHMIC RENDERING OF GRAPHICAL USER INTERFACE ELEMENTS

(71) Applicant: Akili Interactive Labs, Inc., Boston, MA (US)

(72) Inventor: Adam Piper, Petaluma, CA (US)

(73) Assignee: Akili Interactive Labs, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/513,417

(22) Filed: Nov. 17, 2023

(65) Prior Publication Data

US 2024/0086029 A1    Mar. 14, 2024

Related U.S. Application Data

(63) Continuation of application No. 17/948,640, filed on Sep. 20, 2022, now Pat. No. 11,829,571.

(Continued)

(51) Int. Cl.
*G06F 3/0481* (2022.01)
*G06F 11/34* (2006.01)

(52) U.S. Cl.
CPC ........ *G06F 3/0481* (2013.01); *G06F 11/3495* (2013.01)

(58) Field of Classification Search
CPC .... G06F 3/04842; G06F 3/016; G06F 3/0481; G06F 3/04845; G06F 3/0482; G06T 2200/24
See application file for complete search history.

(56) References Cited

U.S. PATENT DOCUMENTS 8,191,007 B1 * 5/2012 Veloz, III .............. G06F 16/957
                                                      715/842
2020/0174557 A1 * 6/2020 Alailima .............. A61B 5/4884

OTHER PUBLICATIONS

Li Liu et al., FiTouch: Adapting Graphical User Interface for Touch Interaction, Oct. 1, 2014, IEEE International Symposium on Haptic, Audio and Visual Environments and Games, pp. 88-93 (Year: 2014).*

(Continued)

*Primary Examiner* — Tam T Tran
(74) *Attorney, Agent, or Firm* — Gregory Finch; Finch Paolino, LLC

(57) ABSTRACT

A system and method for algorithmically modifying, in real-time, one or more graphical user elements of an end user application for a SaMD or DHI product/platform. The method may enable real-time modification of a graphical user interface in response to determining that one or more user-generated responses in response to one or more CSIs are reflective of a targeted stimulus-response pattern. The targeted stimulus-response pattern may reflect a threshold of active therapeutic delivery for the SaMD or DHI to the end user. The method of algorithmically modifying the one or more graphical user elements may include rendering new elements or modifying existing elements, including changing the color of existing elements, for only the time period when the user-generated responses are reflective of the targeted stimulus-response pattern and/or for a pre-determined period of time before and/or after the user-generated responses are reflective of the targeted stimulus-response pattern.

20 Claims, 12 Drawing Sheets
(5 of 12 Drawing Sheet(s) Filed in Color)

Related U.S. Application Data

(60) Provisional application No. 63/246,230, filed on Sep. 20, 2021.

(56) References Cited

OTHER PUBLICATIONS

Yang Yongzhi et al., Automatic User Interface Generating for Simple Interaction in Pervasive Computing, Jul. 1, 2017, IEEE International Conference on Computational Science and Engineering, pp. 1-6 (Year: 2017).*

* cited by examiner

SYSTEMS AND METHOD FOR ALGORITHMIC RENDERING OF GRAPHICAL USER INTERFACE ELEMENTS

CROSS-REFERENCE TO RELATED APPLICATIONS

This application is a continuation of U.S. patent application Ser. No. 17/948,640, filed on Sep. 20, 2022, entitled "SYSTEM AND METHOD FOR ALGORITHMIC RENDERING OF GRAPHICAL USER INTERFACE ELEMENTS"; which claims priority benefit of U.S. Provisional Application Ser. No. 63/246,230, filed Sep. 20, 2021, entitled "METHOD FOR ALGORITHMIC RENDERING OF GRAPHICAL USER INTERFACE ELEMENTS"; the entireties of which are hereby incorporated herein at least by virtue of this reference.

FIELD

The present disclosure relates to the field of graphical user interfaces in computer program products; in particular, methods for algorithmically rendering graphical user interface elements in SaMD products.

BACKGROUND

Software is an increasingly critical area of healthcare product development. An expanding area of healthcare product development is in the area of digital health interventions (i.e., interventions delivered via digital technologies such as smartphones, mobile computing devices, wearable electronic devices, and the like) to provide effective, cost-effective, safe, and scalable interventions to improve health and healthcare. Digital health interventions (DHI) and Software as a Medical Device (SaMD) can be used to promote healthy behaviors, improve outcomes in people with long term conditions such as cardiovascular disease, diabetes and mental health conditions and provide remote access to effective treatments; for example, computerized cognitive behavioral therapy for mental health and somatic problems. Software as a Medical Device (SaMD) is defined by the International Medical Device Regulators Forum (IMDRF) as "software intended to be used for one or more medical purposes that perform these purposes without being part of a hardware medical device." DHIs are often complex interventions with multiple components, and many have multiple aims including enabling users to be better informed about their health, share experiences with others in similar positions, change perceptions and cognitions around health, assess and monitor specified health states or health behaviors, titrate medication, clarify health priorities and reach treatment decisions congruent with these, and improve communication between patients and health care professionals (HCP). Active components may include information, psychoeducation, personal stories, formal decision aids, behavior change support, interactions with HCP and other patients, self-assessment or monitoring tools (questionnaires, wearables, monitors, and effective theory-based psychological interventions developed for face-to-face delivery such as cognitive behavioral therapy or mindfulness training). Certain DHI and SaMD products may include software that is itself directly therapeutically active in treating and/or targeting one or more neurological circuits related to one or more neurological, psychological and/or somatic conditions, diseases, and/or disorders, rather than just being a component of overall treatment.

SUMMARY

In order to provide a basic understanding of the invention, the following is a simplified summary of certain embodiments thereof. This summary is not extensive and is not intended to identify key/critical elements of the invention or to delineate the scope of the invention. Its sole purpose is to present embodiments of the invention in a simplified form as a prelude to the more detailed description that is further below.

Certain aspects of the present disclosure provide for a computer-implemented method for modifying a graphical user interface at an end user device, the computer-implemented method comprising presenting, with at least one processor, an instance of an end user application to an end user, the end user application comprising the graphical user interface at a display of the end user device, wherein the end user application comprises one or more computerized stimuli or interactions comprising at least two computerized tasks; receiving, with at least one input device of the end user device, a plurality of user-generated responses in response to the one or more computerized stimuli or interactions; analyzing, with the at least one processor, the plurality of user-generated responses according to a predetermined stimulus-response framework or algorithm; determining, with the at least one processor, a measure of time-near-threshold or time-at-threshold according to the predetermined stimulus-response framework or algorithm for the end user within the instance of the end user application; modifying, with the at least one processor, one or more graphical elements of the graphical user interface in response to determining the measure of time-near-threshold or time-at-threshold for the end user within the instance of the end user application; and restoring, with the at least one processor, the graphical user interface to a state prior to modifying the one or more graphical elements.

In accordance with certain embodiments, the computer-implemented method may be configured wherein modifying the one or more graphical elements comprises adding or removing one or more graphical elements within the graphical user interface. In certain embodiments, modifying the one or more graphical elements may comprise rendering a portion of the graphical user interface in grayscale. In accordance with certain aspects of the present disclosure, the predetermined stimulus-response framework or algorithm is reflective of a threshold of active therapeutic delivery to the end user within the instance of the end user application. The computer-implemented method may further comprise one or more steps or operations for calculating, with the at least one processor, a first baseline performance measure for the end user, wherein the first baseline performance measure comprises a first quantitative measure of user performance for performing each task in the at least two computerized tasks in isolation. The computer-implemented method may further comprise one or more steps or operations for calculating, with the at least one processor, a second baseline performance measure for the end user, wherein the second baseline performance measure comprises a second quantitative measure of user performance for performing the at least two computerized tasks concurrently or concomitantly. In certain embodiments, determining the measure of time-near-threshold or time-at-threshold may further comprise calculating a difference between the first baseline performance measure and the second baseline performance measure. Determining the measure of time-near-threshold or time-at-threshold may further comprise determining a measure of incremental improvement to the second baseline performance measure for the end user. In accordance with certain aspects of the present disclosure, the measure of time-near-threshold or time-at-threshold may be increased at two or more increments within the instance of the end user application. In certain embodiments, modifying the one or more graphical elements may comprise adding or modifying at least one graphical element configured to indicate that the end user has achieved the measure of time-near-threshold or time-at-threshold.

Further aspects of the present disclosure provide for a computer-implemented system comprising an end user device comprising a display and at least one input device; a processor operably engaged with the end user device to render a graphical user interface of an end user application at the display; and a non-transitory computer readable medium operably engaged with the processor, the non-transitory computer-readable medium comprising one or more processor-executable instructions stored thereon that, when executed, command the processor to perform one or more operations, the one or more operations comprising presenting an instance of the end user application comprising the graphical user interface at the display of the end user device, wherein the end user application comprises one or more computerized stimuli or interactions comprising at least two computerized tasks; receiving, via the at least one input device, a plurality of user-generated responses in response to the one or more computerized stimuli or interactions; analyzing the plurality of user-generated responses according to a predetermined stimulus-response framework or algorithm; determining a measure of time-near-threshold or time-at-threshold according to the predetermined stimulus-response framework or algorithm for an end user within the instance of the end user application; modifying one or more graphical elements of the graphical user interface in response to determining the measure of time-near-threshold or time-at-threshold for the end user within the instance of the end user application; and restoring the graphical user interface to a state prior to modifying the one or more graphical elements.

A non-transitory computer-readable medium with one or more processor-executable instructions stored thereon that, when executed, command one or more processors to perform one or more operations, the one or more operations comprising presenting an instance of an end user application comprising a graphical user interface at a display of an end user device, wherein the end user application comprises one or more computerized stimuli or interactions comprising at least two computerized tasks; receiving, via at least one input device, a plurality of user-generated responses in response to the one or more computerized stimuli or interactions; analyzing the plurality of user-generated responses according to a predetermined stimulus-response framework or algorithm; determining a measure of time-near-threshold or time-at-threshold according to the predetermined stimulus-response framework or algorithm for an end user within the instance of the end user application; modifying one or more graphical elements of the graphical user interface in response to determining the measure of time-near-threshold or time-at-threshold for the end user within the instance of the end user application; and restoring the graphical user interface to a state prior to modifying the one or more graphical elements.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be recognized by those skilled in the art that such equivalent structures do not depart from the spirit and scope of the invention.

BRIEF DESCRIPTION OF DRAWINGS

The patent or application file contains at least one drawing executed in color. Copies of this patent or patent application publication with color drawing(s) will be provided by the Office upon request and payment of the necessary fee.

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

Figure 1:
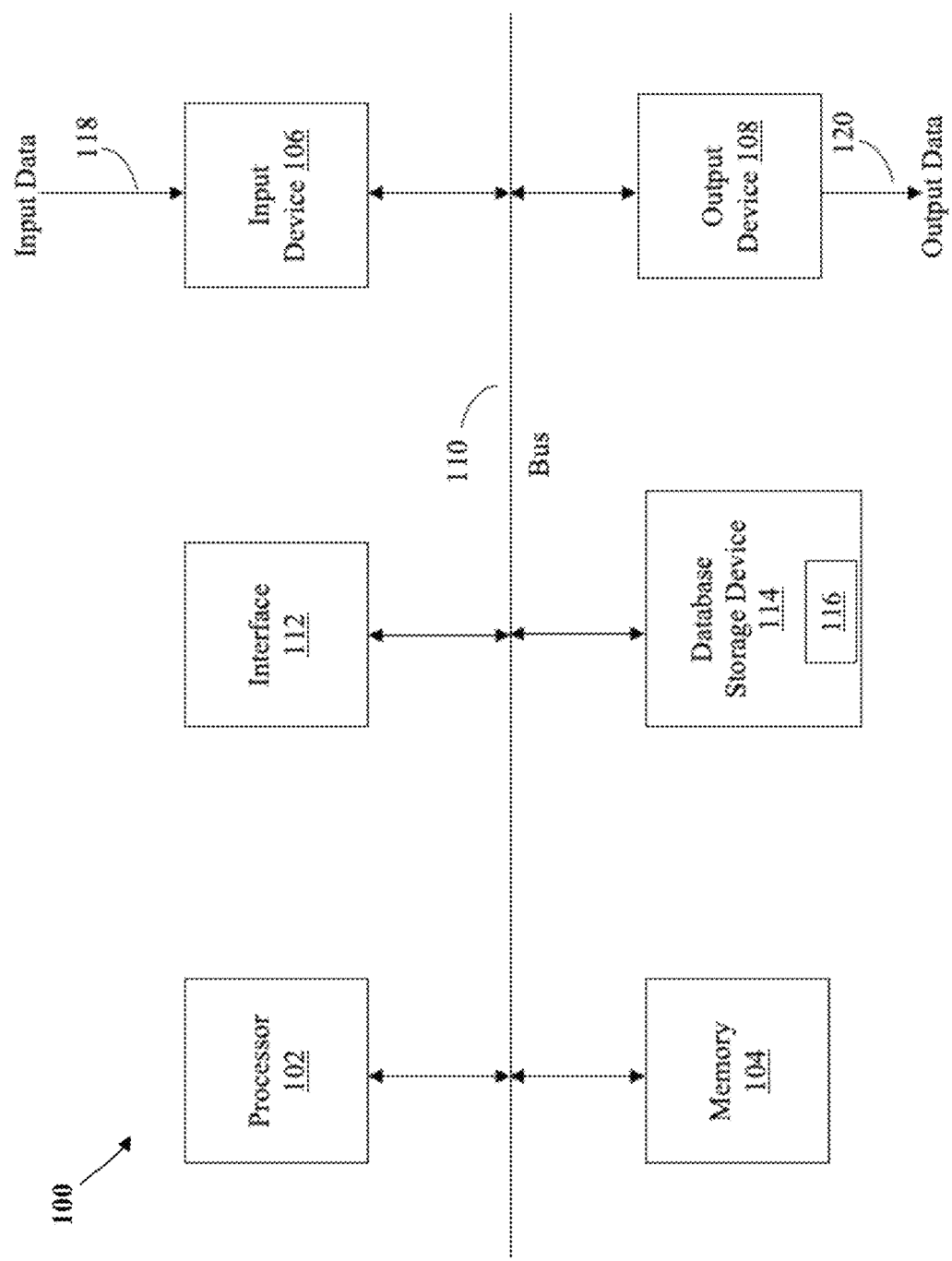
FIG. 1 is a functional block diagram of an exemplary computing system through which certain aspects of the present disclosure may be implemented.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, devices, systems and non-transitory computer-readable media having instructions stored thereon to enable one or more said methods, devices and systems for modifying a graphical user interface at an end user device, comprising presenting an instance of an end user application comprising the graphical user interface at a display of the end user device, wherein the end user application comprises one or more computerized stimuli or interactions; receiving a plurality of user-generated responses in response to the one or more computerized stimuli or interactions; analyzing the plurality of user-generated responses according to a predetermined stimulus-response framework or algorithm, wherein the predetermined stimulus-response framework or algorithm is reflective of a threshold of active therapeutic delivery to the end user within the instance of the end user application; determining a measure of time-near-threshold or time-at-threshold according to the predetermined stimulus-response framework or algorithm for the end user within the instance of the end user application; modifying one or more graphical elements of the graphical user interface in response to determining the time-near-threshold or time-at-threshold for the end user within the instance of the end user application, wherein modifying the one or more graphical elements comprises adding or removing one or more graphical elements within the graphical user interface or rendering a portion of the graphical user interface in grayscale; and restoring the graphical user interface to a state prior to modifying the one or more graphical elements.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The present disclosure should in no way be limited to the exemplary implementation and techniques illustrated in the drawings and described below.

Where a range of values is provided, it is understood that each intervening value, to the tenth of the unit of the lower limit unless the context clearly dictates otherwise, between the upper and lower limit of that range and any other stated or intervening value in that stated range is encompassed by the invention. The upper and lower limits of these smaller ranges may independently be included in the smaller ranges, and are also encompassed by the invention, subject to any specifically excluded limit in a stated range. Where a stated range includes one or both of the endpoint limits, ranges excluding either or both of those included endpoints are also included in the scope of the invention.

As used herein, "exemplary" means serving as an example or illustration and does not necessarily denote ideal or best.

As used herein, the term "includes" means includes but is not limited to, the term "including" means including but not limited to. The term "based on" means based at least in part on.

As used herein, the term "stimulus" refers to a sensory event configured to evoke a specified functional response from an individual. The degree and type of response can be quantified based on the individual's interactions with a measuring component (including using sensor devices or other measuring components).

As used in certain examples herein, the term "user activity data" refers to data collected from measures of an interaction of a user with a software program, product and/or platform.

As used herein, the term "computerized stimuli or interaction" or "CSI" refers to a computerized element that is presented to a user to facilitate the user's interaction with a stimulus or other interaction. As non-limiting examples, the computing device can be configured to present auditory stimulus (presented, e.g., as an auditory computerized adjustable element or an element of a computerized auditory task) or initiate other auditory-based interaction with the user, and/or to present vibrational stimuli (presented, e.g., as a vibrational computerized adjustable element or an element of a computerized vibrational task) or initiate other vibrational-based interaction with the user, and/or to present tactile stimuli (presented, e.g., as a tactile computerized adjustable element or an element of a computerized tactile task) or initiate other tactile-based interaction with the user, and/or to present visual stimuli or initiate other visual-based interaction with the user.

In an example where the computing device is configured to present visual CSI, the CSI can be rendered as at least one user interface to be presented to a user. In some examples, the at least one user interface is configured for measuring responses as the user interacts with a CSI computerized element rendered at the at least one user interface. In a non-limiting example, the user interface can be configured such that the CSI computerized element(s) are active, and may require at least one response from a user, such that the user interface is configured to measure data indicative of the type or degree of interaction of the user with the platform product. In another example, the user interface can be configured such that the CSI computerized element(s) are passive and are presented to the user using the at least one user interface but may not require a response from the user. In this example, the at least one user interface can be configured to exclude the recorded response of an interaction of the user, to apply a weighting factor to the data indicative of the response (e.g., to weight the response to lower or higher values), or to measure data indicative of the response of the user with the platform product as a measure of a misdirected response of the user (e.g., to issue a notification or other feedback to the user of the misdirected response).

As used in certain examples herein, the term "user" encompasses one or more of an end user and/or test user of a software program, product and/or platform and may further include: a patient being engaged with a software program, product or platform for a targeted medical or personal wellness purpose; a participant in a clinical trial, study or evaluation of a software program, product or platform; a user being engaged with a software program, product or platform for the purpose of evaluating or developing one or more technical, clinical, and/or functional aspects of a digital health intervention and/or a software as a medical device program, product or platform.

As used herein the terms "digital health intervention (DHI)" and "software as a medical device (SaMD)" may be used interchangeably and encompass any software program, product, or platform, including any software/hardware combination, being designed and/or utilized for any general or targeted medical or personal wellness purpose, including but not limited to the treatment, diagnosis, management, prevention, cure, or generation or provision of clinical, health, and/or wellness insights or recommendations to one or more users for one or more medical, health or personal wellness purpose; including any software program, product, or platform, including any software/hardware combination, being designed and/or utilized to promote healthy behaviors, improve outcomes in people with long term conditions such as cardiovascular disease, diabetes and mental health conditions and provide remote access to effective treatments; for example, computerized cognitive behavioral therapy for mental health and somatic problems; and may further encompass one or more software program, product or platform, including any product(s), program(s) and/or platform(s) that incorporate any combination of hardware and software, that is/are directly therapeutically active in treating and/or targeting one or more neurological circuits related to one or more neurological, psychological and/or somatic conditions, diseases, and/or disorders, rather than just being a component of overall treatment.

All definitions, as defined and used herein, should be understood to control over dictionary definitions, definitions in documents incorporated by reference, and/or ordinary meanings of the defined terms. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

An exemplary system, method, and non-transitory computer readable media according to the principles herein provides for a method of algorithmically modifying, in real-time, one or more graphical user elements of an end user application for a SaMD or DHI product/platform. In certain embodiments, the method may enable real-time modification of a graphical user interface in response to determining that one or more user-generated responses in response to one or more CSIs are reflective of a targeted stimulus-response pattern; more particularly, a therapeutically active stimulus-response pattern. In accordance with certain aspects of the present disclosure, the targeted stimulus-response pattern may reflect a threshold of active therapeutic delivery for the SaMD or DHI to the end user. In certain embodiments, the method of algorithmically modifying the one or more graphical user elements may include rendering new elements or modifying existing elements, including changing the color of existing elements, for only the time period when the user-generated responses are reflective of the targeted stimulus-response pattern (i.e., time at therapeutic threshold) and/or for a pre-determined period of time before and/or after the user-generated responses are reflective of the targeted stimulus-response pattern (i.e., time near therapeutic threshold).

An exemplary system, method, and non-transitory computer readable media according to the principles herein provides for a method of algorithmically modifying one or more graphical user elements of an interactive video game in real-time in response to determining that one or more user-generated responses in response to one or more CSIs are reflective of a targeted stimulus-response pattern. In certain embodiments, the method of algorithmically modifying the one or more graphical user elements may include rendering new elements or modifying existing elements, including changing the color of existing elements, for only the time period when the user-generated responses are reflective of the targeted stimulus-response pattern and/or for a pre-determined period of time before and/or after the user-generated responses are reflective of the targeted stimulus-response pattern.

Turning now descriptively to the drawings, in which similar reference characters denote similar elements throughout the several views, FIG. 1 depicts a computing system in which certain illustrated embodiments of the present invention may be implemented.

Referring now to FIG. 1, a processor-implemented computing device in which one or more aspects of the present disclosure may be implemented is shown. According to an embodiment, a processing system 100 may generally comprise at least one processor 102, a memory 104, an input device 106 for receiving input data 118 and an output device 108 that produces output data 120 coupled together with at least one bus 110. In certain embodiments, input device 106 and output device 108 could be the same device. An interface 112 can also be provided for coupling the processing system 100 to one or more peripheral devices, for example interface 112 could be a PCI card or PC card. At least one database storage device 114 which houses at least one database 116 can also be provided. The memory 104 can be any form of memory device, for example, volatile or non-volatile memory, solid state storage devices, magnetic devices, etc. The processor 102 could comprise more than one distinct processing device, for example to handle different functions within the processing system 100. Input device 106 receives input data 118 and can comprise, for example, a keyboard, a pointer device such as a pen-like device or a mouse, audio receiving device for voice-controlled activation such as a microphone, data receiver or antenna such as a modem or wireless data adaptor, data acquisition card, etc. Input data 118 could come from different sources, for example keyboard instructions in conjunction with data received via a network. Output device 108 produces or generates output data 120 and can comprise, for example, a display device or monitor in which case output data 120 is visual, a printer in which case output data 120 is printed, a port for example a USB port, a peripheral component adaptor, a data transmitter or antenna such as a modem or wireless network adaptor, etc. Output data 120 could be distinct and derived from different output devices, for example a visual display on a monitor in conjunction with data transmitted to a network. A user could view data output, or an interpretation of the data output, on, for example, a monitor or using a printer. The storage device 114 can be any form of data or information storage means, for example, volatile or non-volatile memory, solid state storage devices, magnetic devices, and the like.

In use, the processing system 100 is adapted to allow data or information to be stored in and/or retrieved from, via wired or wireless communication means, at least one database 116. The interface 112 may allow wired and/or wireless communication between the processing unit 102 and peripheral components that may serve a specialized purpose. In general, the processor 102 can receive instructions as input data 118 via input device 106 and can display processed results or other output to a user by utilizing output device 108. More than one input device 106 and/or output device 108 can be provided. It should be appreciated that the processing system 100 may be any form of terminal, server, specialized hardware, or the like.

It is to be appreciated that the processing system 100 may be a part of a networked communications system. Processing system 100 could connect to a network, for example the Internet or a WAN. Input data 118 and output data 120 could be communicated to other devices via the network. The transfer of information and/or data over the network can be achieved using wired communications means or wireless communications means. A server can facilitate the transfer of data between the network and one or more databases. A server and one or more databases provide an example of an information source.

Thus, the processing computing system environment 100 illustrated in FIG. 1 may operate in a networked environment using logical connections to one or more remote computers. The remote computer may be a personal computer, a server, a router, a network PC, a peer device, or other common network node, and typically includes many or all of the elements described above.

It is to be further appreciated that the logical connections depicted in FIG. 1 include a local area network (LAN) and a wide area network (WAN) but may also include other networks such as a personal area network (PAN). Such networking environments are commonplace in offices, enterprise-wide computer networks, intranets, and the Internet. For instance, when used in a LAN networking environment, the computing system environment 100 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 100, or portions thereof, may be stored in a remote memory storage device. It is to be appreciated that the illustrated network connections of FIG. 1 are exemplary and other means of establishing a communications link between multiple computers may be used.

FIG. 1 is intended to provide a brief, general description of an illustrative and/or suitable exemplary environment in which various embodiments of the invention may be implemented. FIG. 1 is an example of a suitable environment and is not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

In the description that follows, certain embodiments may be described with reference to acts and symbolic representations of operations that are performed by one or more computing devices, such as the computing system 100 of FIG. 1. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments of the present invention can be implemented with numerous other general-purpose or special-purpose computing devices, systems or configurations. Examples of well-known computing systems, environments, and configurations suitable for use in embodiments of the invention include personal computers, handheld or laptop devices, personal digital assistants, multiprocessor systems, microprocessor-based systems, set top boxes, programmable consumer electronics, network, minicomputers, server computers, game server computers, web server computers, mainframe computers, and distributed computing environments that include any of the above systems or devices.

Various embodiments of the invention will be described herein in a general context of computer-executable instructions, such as program modules, being executed by a computer. Generally, program modules include routines, programs, objects, components, data structures, etc., that perform particular tasks or implement particular abstract data types. In certain embodiments, distributed computing environments where tasks are performed by remote processing devices that are linked through a communications network may also be employed. In distributed computing environments, program modules may be located in both local and remote computer storage media including memory storage devices.

With the general computing system environment 100 of FIG. 1 being shown and discussed above, the following description and remaining figures pertain to various exemplary embodiments of the present invention generally relating to methods and systems for modifying a graphical user interface at an end user device within an instance of an end user application (e.g., an SaMD product). In general, the methods described herein involve presenting, with at least one processor, an instance of an end user application comprising the graphical user interface at a display of the end user device, wherein the end user application comprises one or more computerized stimuli or interactions; receiving, with at least one input device of the end user device, a plurality of user-generated responses in response to the one or more computerized stimuli or interactions; analyzing, with the at least one processor, the plurality of user-generated responses according to a predetermined stimulus-response framework or algorithm, wherein the predetermined stimulus-response framework or algorithm is reflective of a threshold of active therapeutic delivery to the end user within the instance of the end user application; determining, with the at least one processor, a measure of time-near-threshold or time-at-threshold according to the predetermined stimulus-response framework or algorithm for the end user within the instance of the end user application; modifying, with the at least one processor, one or more graphical elements of the graphical user interface in response to determining the time-near-threshold or time-at-threshold for the end user within the instance of the end user application, wherein modifying the one or more graphical elements comprises adding or removing one or more graphical elements within the graphical user interface or rendering a portion of the graphical user interface in grayscale; and restoring, with the at least one processor, the graphical user interface to a state prior to modifying the one or more graphical elements.

Figure 2:
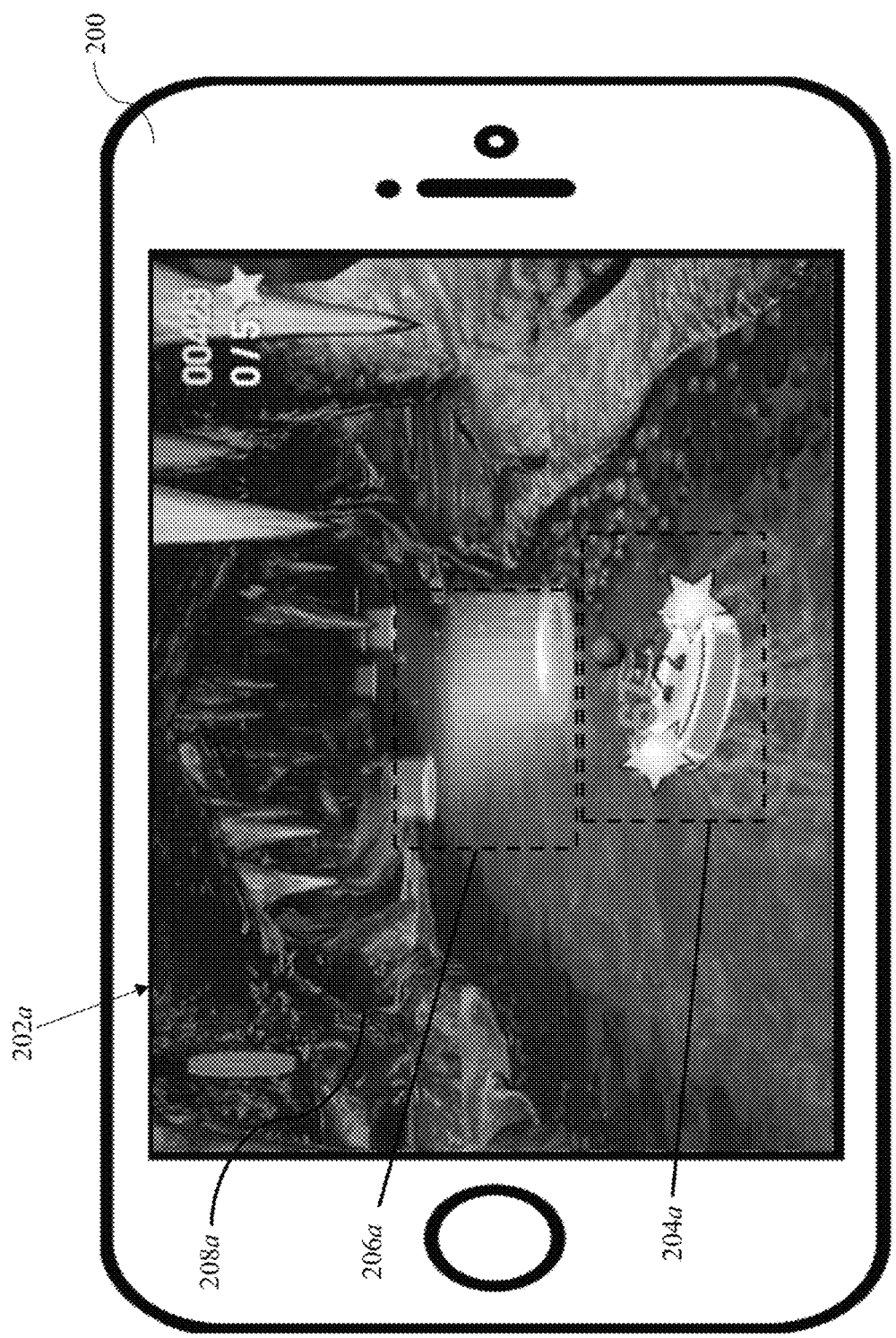
FIG. 2 is a graphical illustration of a graphical user interface rendered at an end user device, in accordance with certain aspects of the present disclosure.

Referring now to FIG. 2, a graphical illustration of a user interface 202a rendered at a display of an end user device 200 is shown. In accordance with certain aspects of the present disclosure, graphical user interface 202a comprises a graphical user interface of an end user application; for example, an interactive video game. In certain embodiments, the end user application comprises a SaMD or DHI product or platform configured to present one or more computerized stimuli or interactions to the end user. In accordance with certain aspects of the present disclosure, the one or more computerized stimuli or interactions may be configured to prompt one or more therapeutically active stimulus-response patterns from the user in response to presenting the one or more computerized stimuli or interactions (CSIs) via the graphical user interface of the end user application. In accordance with certain aspects of the present disclosure, graphical user interface 202a may comprise one or more graphical elements including, but not limited to, a user avatar 204a, a navigation target 206a, and a game level environment 208a. In certain embodiments, game level environment 208a comprises a visuomotor navigation path through which a user is prompted to navigate user avatar 204a near or at navigation target 206a. In accordance with certain aspects of the present disclosure, graphical user interface 202a may be configured to prompt and receive a plurality of user-generated responses in response to the CSIs presented within the instance of the end user application. The plurality of user-generated responses may be analyzed (e.g., with one or more processors communicably engaged with end user device 200) according to one or more algorithms or computational frameworks to determine whether the plurality of user-generated responses reflect a stimulus-response pattern that is at, or near, a therapeutically active threshold according to at least one therapeutic delivery engine; for example, a selective stimulus management engine.

Figure 3:
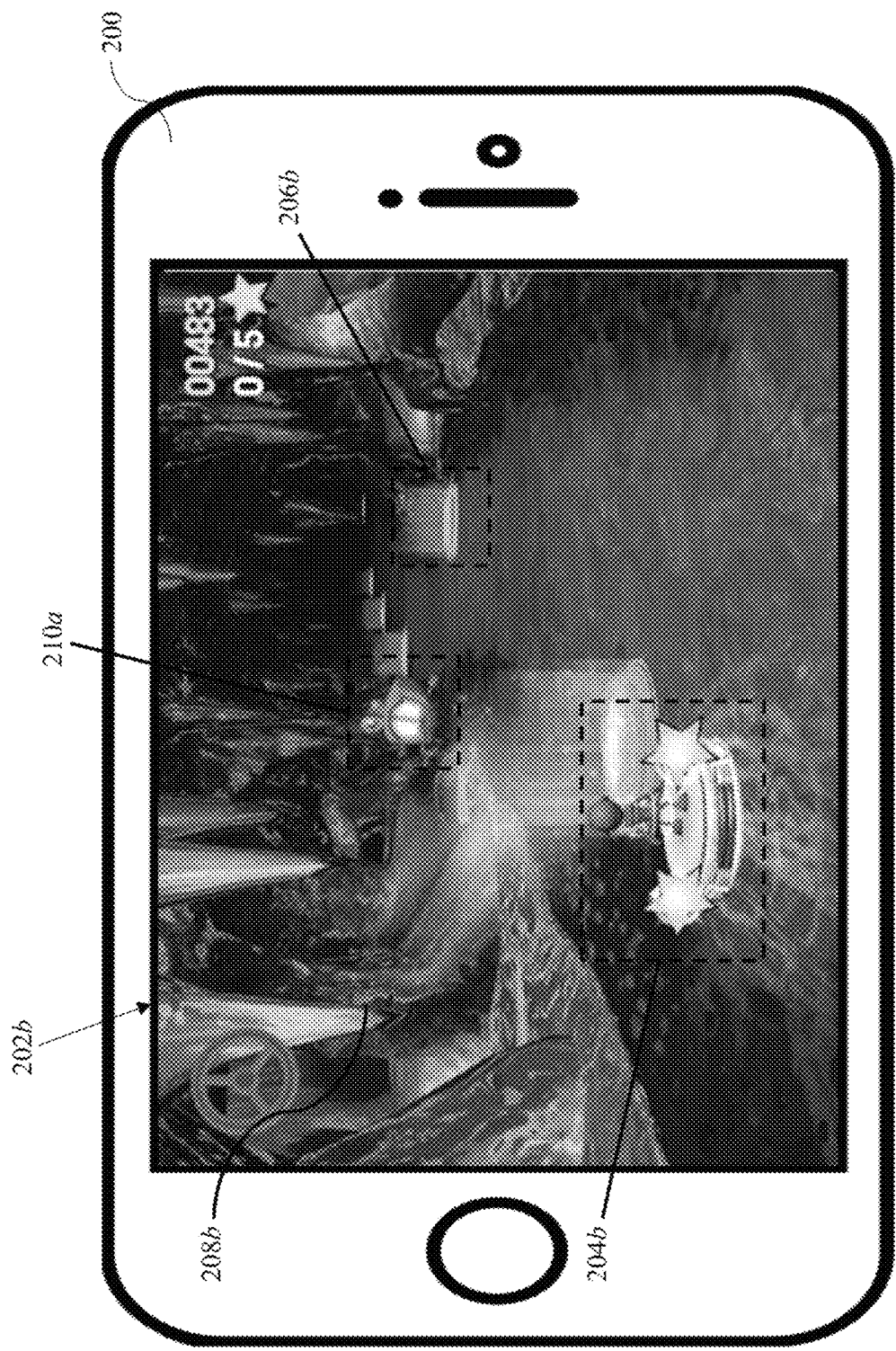
FIG. 3 is a graphical illustration of a graphical user interface rendered at an end user device, in accordance with certain aspects of the present disclosure.

FIG. 3 provides a graphical illustration of a graphical user interface 202b rendered at the display of end user device 200. In accordance with certain aspects of the present disclosure, graphical user interface 202b represents a state change (i.e., progression within the instance of the end user application) of graphical user interface 202a (FIG. 2). In accordance with certain aspects of the present disclosure, graphical user interface 202b may be rendered at the display of end user device 200 in response to determining (e.g., with the one or more processors communicably engaged with end user device 200) that the plurality of user-generated responses received in response to graphical user interface 202a (FIG. 2) are at or near the therapeutically active threshold according to the at least one therapeutic delivery engine. In accordance with certain embodiments, graphical user interface 202b may be configured to render and present, in real-time, at least one graphical interface element 210a in response to the user achieving/maintaining the therapeutically active threshold according to the at least one therapeutic delivery engine for a specified period of time. In accordance with certain embodiments, graphical interface element 210a may comprise a character, object, target or the like within game level environment 208b. In accordance with certain aspects of the present disclosure, graphical user interface 202b may be configured to modify one or more graphical elements of user avatar 204b, navigation target 206b, and/or game level environment 208b in real-time in response to the plurality of user-generated responses received via graphical user interface 202a (FIG. 2) being at or near the therapeutically active threshold.

Figure 4:
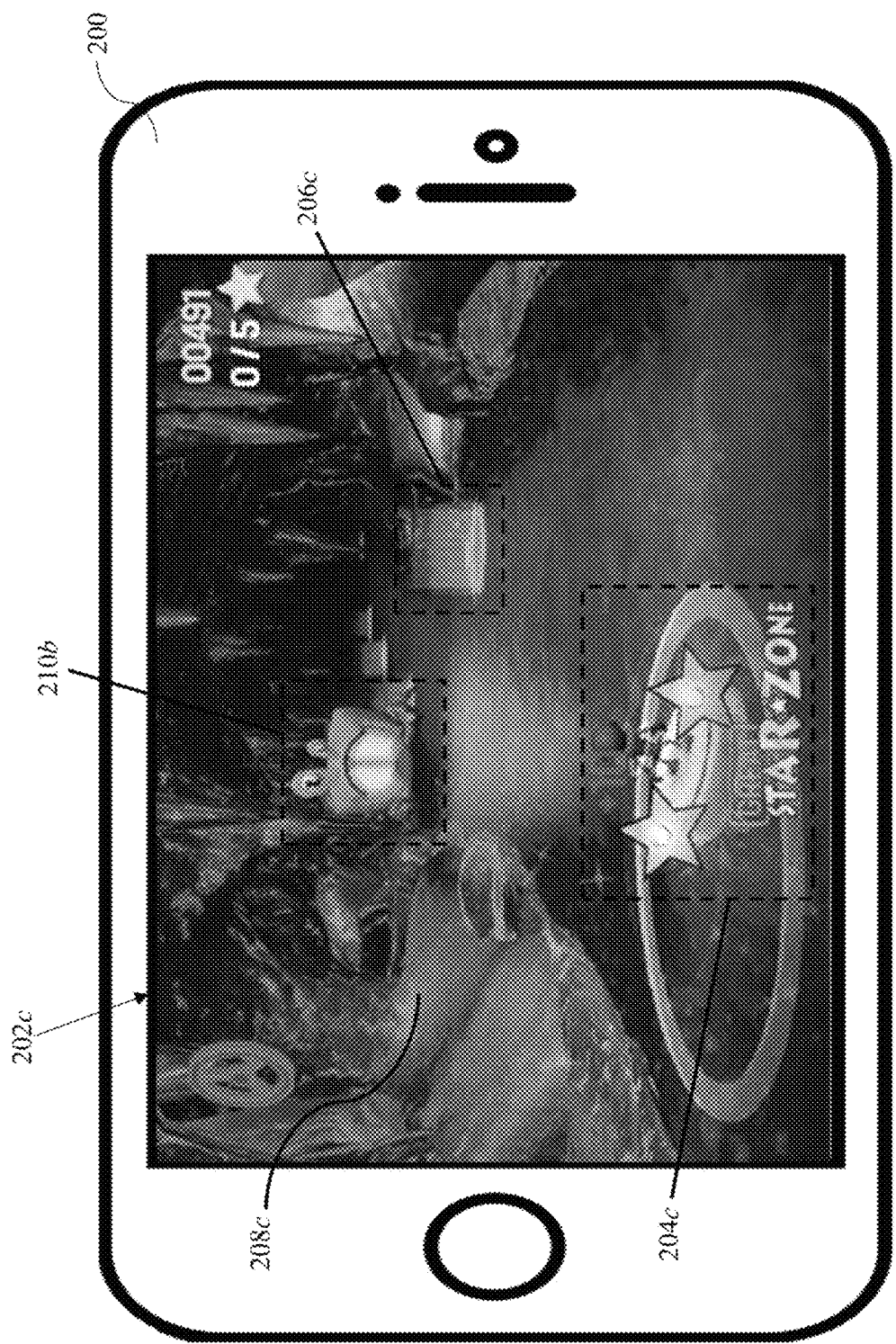
FIG. 4 is a graphical illustration of a graphical user interface rendered at an end user device, in accordance with certain aspects of the present disclosure.

FIG. 4 provides a graphical illustration of a graphical user interface 202c rendered at the display of end user device 200. In accordance with certain aspects of the present disclosure, graphical user interface 202c represents a state change (i.e., progression within the instance of the end user application) of graphical user interface 202b (FIG. 3). In accordance with certain aspects of the present disclosure, user-generated responses received in response to graphical user interface 202b (FIG. 3) may be analyzed (e.g., with the one or more processors communicably engaged with end user device 200) according to the one or more algorithms and/or computational frameworks to determine whether the plurality of user-generated responses are at, or near, the therapeutically active threshold. In accordance with certain aspects of the present disclosure, graphical user interface 202c may be configured to modify graphical interface element 210b in real-time in response to the plurality of user-generated responses being at or near the therapeutically active threshold. In certain embodiments, graphical user interface 202c may render a size, shape, color and/or display or animation of graphical interface element 210b in response to the plurality of user-generated responses being at or near the therapeutically active threshold. In accordance with certain aspects of the present disclosure, graphical user interface 202c may be configured to modify one or more graphical elements of user avatar 204c, navigation target 206c, and/or game level environment 208c in real-time in response to the plurality of user-generated responses received via graphical user interface 202b (FIG. 3) being at or near the therapeutically active threshold.

Figure 5:
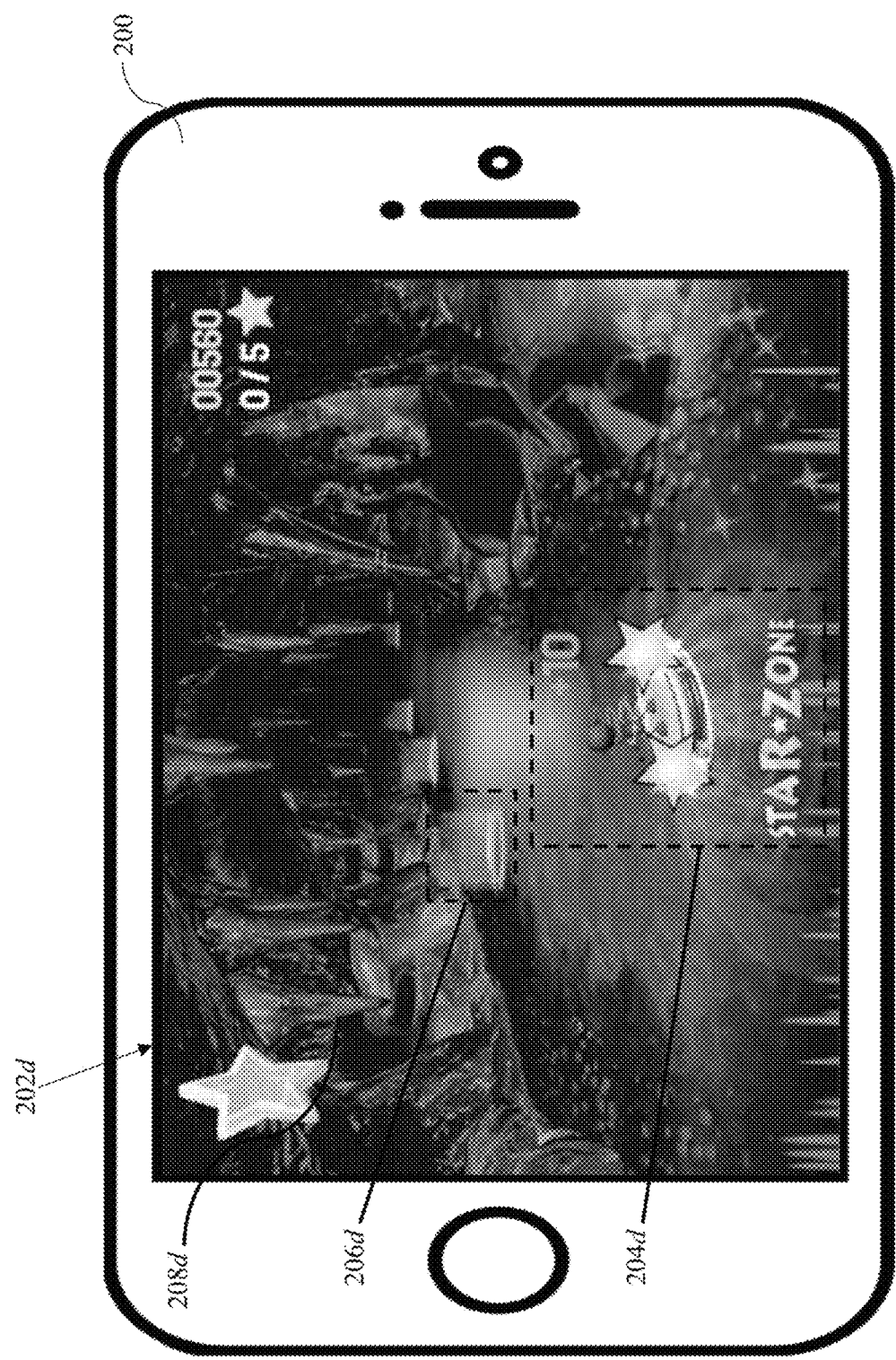
FIG. 5 is a graphical illustration of a graphical user interface rendered at an end user device, in accordance with certain aspects of the present disclosure.

FIG. 5 provides a graphical illustration of a graphical user interface 202d rendered at the display of end user device 200. In accordance with certain aspects of the present disclosure, graphical user interface 202d represents a state change (i.e., progression within the instance of the end user application) of any of graphical user interfaces 202a-c (FIG. 2-4) in which the plurality of user-generated responses received via any of graphical user interfaces 202a-c (FIG. 2-4) are at or above the therapeutically active threshold according to at least one therapeutic delivery engine; for example, a selective stimulus management engine. In accordance with certain embodiments, graphical user interface 202d is configured to selectively modify one or more color elements or schemes of graphical user interface 202d in response to a measure of user performance (as determined by the at least one therapeutic delivery engine) being at or above the therapeutically active threshold. In accordance with certain embodiments, graphical user interface 202d is configured to modify, in real-time, one or more color elements or schemes of game level environment 208d such that one or more therapeutically active elements/interactions (e.g., user avatar 204d and navigation target 206d) of graphical user interface 202d are emphasized, while inactive/ornamental elements of graphical user interface 202d (e.g., game level environment 208d) are de-emphasized (e.g., grayscale). In accordance with certain aspects of the present disclosure, graphical user interface 202d may be modified in real-time in order to increase user focus and attention on the one or more therapeutically active elements/interactions of graphical user interface 202d for a specified period of time and/or for a period of time in which the user-generated responses are computed as being reflective of desired stimulus-response patterns.

Figure 6:
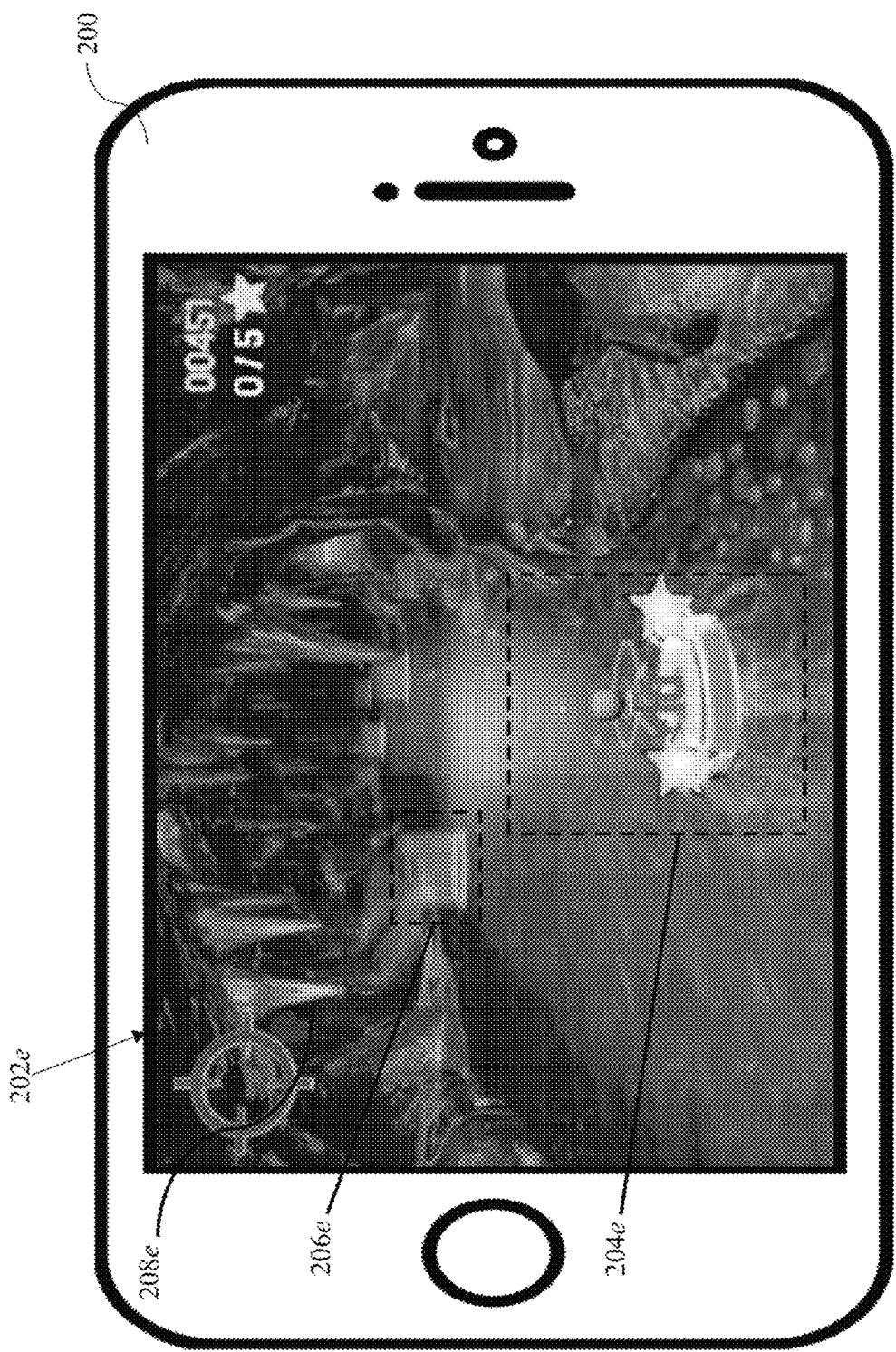
FIG. 6 is a graphical illustration of a graphical user interface rendered at an end user device, in accordance with certain aspects of the present disclosure.

FIG. 6 provides a graphical illustration of a graphical user interface 202e rendered at the display of end user device 200. In accordance with certain aspects of the present disclosure, graphical user interface 202e represents a state change (i.e., progression within the instance of the end user application) of graphical user interface 202d (FIG. 5). In accordance with certain aspects of the present disclosure, graphical user interface 202e is rendered in real-time in response to an expiration of the specified time period of graphical user interface 202d (FIG. 5) and/or in response to the user-generated responses being below a designated stimulus-response pattern threshold. In certain embodiments, graphical user interface 202e may represent a base level or default state of the one or more graphical elements (e.g., user avatar 204e, navigation target 206e, and game level environment 208e) within the instance of the end user application.

Figure 7:
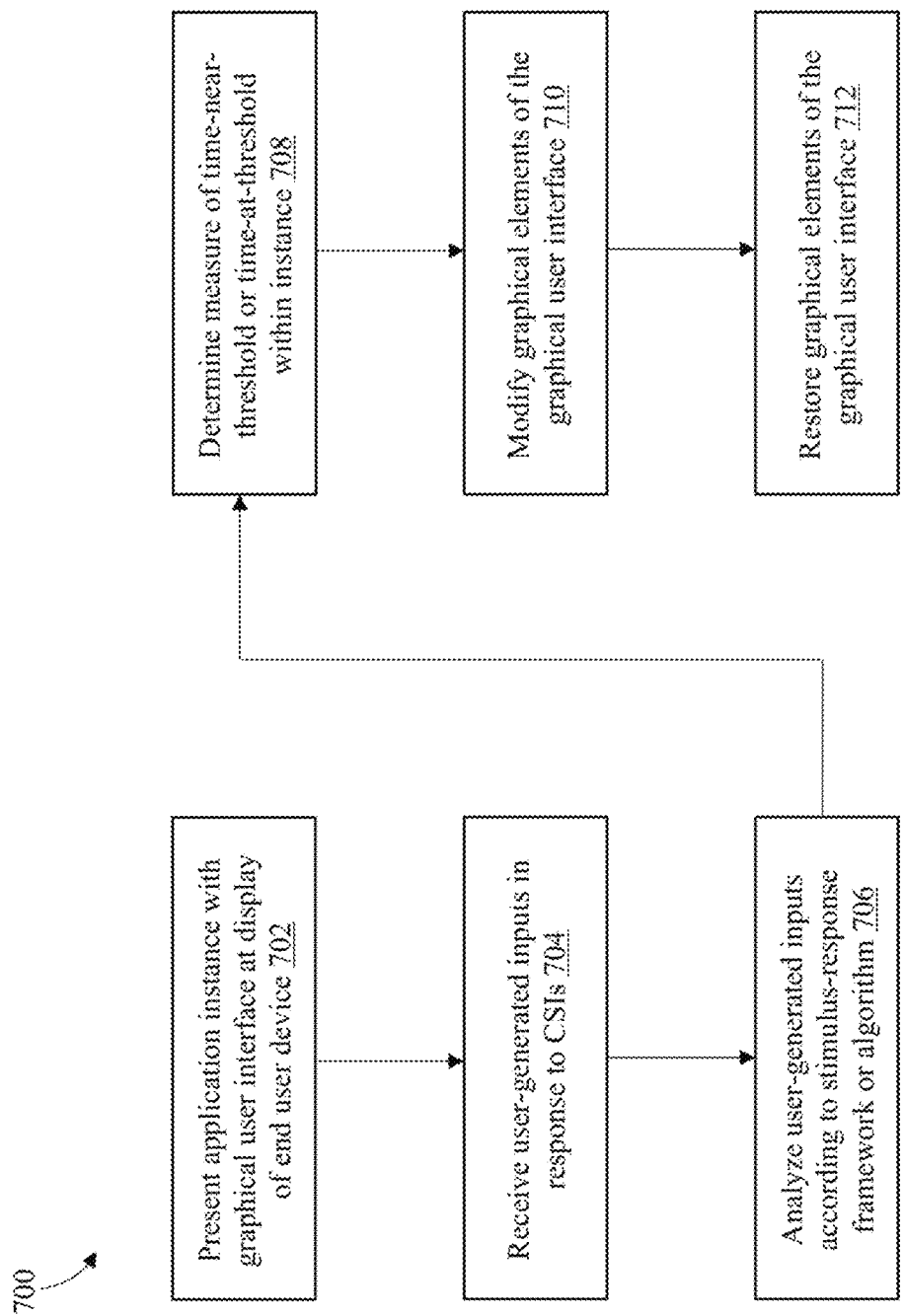
FIG. 7 is a process flow diagram of a method for algorithmically rendering graphical user interface elements in an SaMD product, in accordance with certain aspects of the present disclosure.

Referring now to FIG. 7, a process flow diagram of a method 700 for algorithmically rendering graphical user interface elements in an SaMD product is shown. In accordance with certain aspects of the present disclosure, method 700 comprises one or more steps or operations for modifying a graphical user interface at an end user device; for example, graphical user interface 202 displayed on end user device 200, as shown in FIGS. 2-6. In accordance with certain aspects of the present disclosure, method 700 may comprise one or more steps or operations for presenting (e.g., with at least one processor) an instance of an end user application comprising the graphical user interface at a display of the end user device (Step 702). In certain embodiments, the end user application may comprise one or more computerized stimuli or interactions. In accordance with certain aspects of the present disclosure, the one or more computerized stimuli or interactions are incorporated into an SaMD or DHI product, platform or application. In accordance with certain aspects of the present disclosure, method 700 may proceed by executing one or more steps or operations for receiving (e.g., with at least one input device of the end user device) a plurality of user-generated responses in response to the one or more computerized stimuli or interactions (Step 704). In accordance with certain aspects of the present disclosure, method 700 may proceed by executing one or more steps or operations for analyzing (e.g., with the at least one processor) the plurality of user-generated responses according to a predetermined stimulus-response framework or algorithm (Step 706). In accordance with certain aspects of the present disclosure, the predetermined stimulus-response framework or algorithm is reflective of a threshold of active therapeutic delivery to the end user within the instance of the end user application.

Still referring to FIG. 7, and in accordance with certain aspects of the present disclosure, method 700 may proceed by executing one or more steps or operations for determining (e.g., with the at least one processor) a measure of time-near-threshold or time-at-threshold according to the predetermined stimulus-response framework or algorithm for the end user within the instance of the end user application (Step 708). In accordance with certain aspects of the present disclosure, method 700 may proceed by executing one or more steps or operations for modifying (e.g., with the at least one processor) one or more graphical elements of the graphical user interface in response to determining the time-near-threshold or time-at-threshold for the end user within the instance of the end user application (Step 710). In accordance with certain aspects of the present disclosure, the one or more steps or operations for modifying the one or more graphical elements may comprise one or more steps or operations for adding or removing one or more graphical elements within the graphical user interface or rendering a portion of the graphical user interface in grayscale. In accordance with certain aspects of the present disclosure, method 700 may proceed by executing one or more steps or operations for restoring (e.g., with the at least one processor) the graphical user interface to a state prior to modifying the one or more graphical elements (Step 712).

Figure 8:
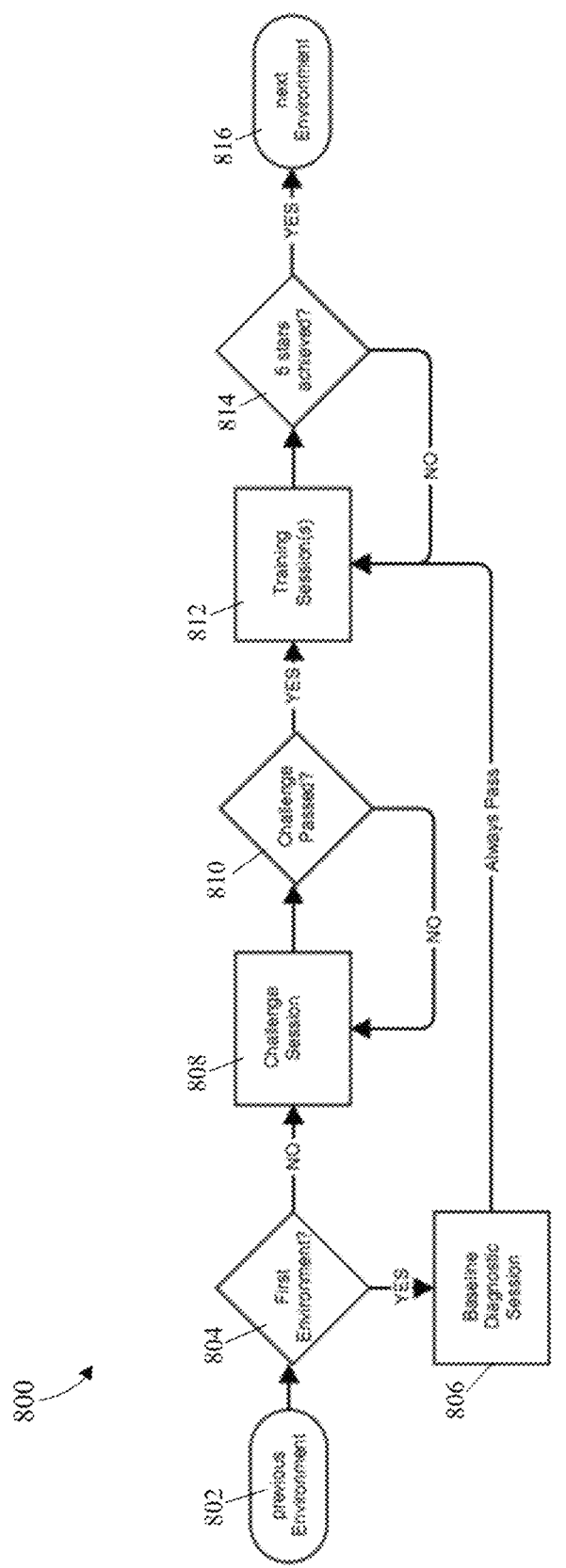
FIG. 8 is a process flow diagram of a routine for rendering a sequence of computerized stimuli or interactions associated with an SaMD product, in accordance with certain aspects of the present disclosure.

Referring now to FIG. 8, a process flow diagram of a routine 800 for rendering a sequence of computerized stimuli or interactions associated with an SaMD product is shown. In accordance with certain aspects of the present disclosure, routine 800 may be incorporated in one or more steps or operations of method 700, as shown in FIG. 7. In accordance with certain embodiments, an SaMD product may comprise an end user application comprising one or more computerized environments in which the one or more computerized stimuli or interactions (CSIs) may be rendered at a display of a user device (e.g., across one or more sessions of the end user application). In certain embodiments, the one or more computerized environments may be embodied within one or more of graphical user interfaces 202a-e, as shown in FIGS. 2-6. In accordance with various aspects of the present disclosure, the CSIs may comprise a first task and a second task, which may be presented to a user via the graphical user interface separately or in isolation (e.g., single tasking) or concurrently/concomitantly (e.g., multi-tasking). In accordance with certain embodiments, the first task may comprise a targeting task (e.g., target discrimination) and the second task may comprise a navigation task (e.g., a visuomotor tracking task). In accordance with certain embodiments, a navigation task may comprise steering a virtual vehicle through a winding course while avoiding obstacles and collecting rewards. The parameters by which obstacles and rewards are presented to the end user may vary in difficulty throughout the session of the end user application. In accordance with certain embodiments, the end user must tilt an end user device left and right to steer a graphical user interface element (e.g., a vehicle) left and right within the graphical user interface. When the end user correctly navigates to a specified area, one or more visual and audio effects may be rendered at the user interface to indicate success. When the end user incorrectly navigates into an obstacle or outside of a specified area, or fails to navigate into a reward, one or more visual and audio effects may be rendered at the user interface to indicate failure. As the end user navigates successfully, obstacles/rewards may be presented more quickly; as the end user fails to navigate successfully, subsequent obstacles/rewards may be presented more slowly. In accordance with certain embodiments, a targeting task may comprise one or more CSIs configured to prompt the end user to discriminate between "correct" and "incorrect" targets. Targets comprising one or more feature that defines a "correct" target may be presented to the end user via the one or more CSIs. The properties that define a "correct" target vary in difficulty throughout the course of a progression of the end user application. In certain embodiments, the one or more CSIs may be configured to prompt the end user to touch the screen when a correct target is presented and ignore any incorrect targets. When the end user taps on a correct target, visual and audio effects may be rendered at the user interface to indicate success. When the end user taps on an incorrect target, or fails to tap on a correct target, visual and audio effects may be rendered at the user interface to indicate failure. In accordance with certain embodiments, the CSIs may comprise one or more multi-tasking prompts in which the end user is prompted to perform the targeting task and the navigation task concurrently or concomitantly. In accordance with certain aspects of the present disclosure, the one or more computerized environments may be rendered based on performance of an end user in a current or prior session of the end user application. One or more graphical user interface elements of the CSIs may be algorithmically (e.g., dynamically) rendered within the session of the end user application based on a performance of the end user at the first and second task within one or more discrete time periods.

In accordance with certain aspects of the present disclosure, a session of an end user application may be instantiated at an end user device upon rendering a previous environment within the instance of the end user application (Step 802). The previous environment may be a computerized environment to which the end user has gained access within prior sessions of the end user application or may constitute the first computerized environment; e.g., if the end user is engaging with the end user application for the first time and/or has not satisfied one or more completion requirements for the first environment in one or more previous sessions and/or if the environment is the first computerized environment in a specific grouping of computerized environments. Routine 800 may comprise one or more steps or operations for determining whether the previous environment, presented in Step 802, is the first environment (Step 804). If YES, routine 800 proceeds to execute one or more steps or operations for presenting a baseline diagnostic session to the end user (Step 806). If NO, routine 800 proceeds to execute one or more steps or operations for presenting a challenge session to the end user (Step 808). In accordance with certain aspects of the present disclosure, a baseline diagnostic session (Step 806) is presented to the end user. The baseline diagnostic session (Step 806) may comprise one or more steps or operations for calculating a first baseline performance measure and a second baseline performance measure for the end user. The first baseline performance measure may comprise a first quantitative measure of the end user's performance in performing each of the two tasks (e.g., targeting and navigation) in isolation. The second baseline performance measure may comprise a first quantitative measure of the end user's performance in performing each of the two tasks concurrently or concomitantly (e.g., multitasking). In certain embodiments, the baseline diagnostic session may comprise four phases of tasks—an initial multitasking phase, a first task in isolation phase, a second task in isolation phase, and a final multitasking phase.

In accordance with certain aspects of the present disclosure, if the output of step 804 is NO, routine 800 may proceed by performing one or more steps or operations for presenting a challenge session to the end user within the computerized environment (Step 808). In certain embodiments, the challenge session (Step 808) comprises the same sequence of CSIs as the baseline diagnostic session—i.e., an initial multitasking phase, a first task in isolation phase, a second task in isolation phase, and a final multitasking phase. In accordance with certain aspects of the present disclosure, the first baseline performance measure and the second baseline performance measure may comprise performance thresholds for the end user for performance at single task CSIs and multitask CSIs in a current or future session of the end user application. Routine 800 may proceed by executing one or more steps or operations to determine whether the end user has satisfied (i.e., passed) one or more parameters for the challenge session (Step 810). Step 810 may comprise one or more steps or operations for comparing the end user's performance on the challenge session to the end user's performance from the baseline diagnostic session and/or comparing the end user's performance on the most recently completed session to one or more previous sessions. In certain embodiments, if the end user's performance thresholds for each task are all at least 90% of their previous values, then the session is passed, otherwise the session is failed. If an output of Step 810 is YES, e.g., the end user has passed the challenge session, then routine 800 may proceed by executing one or more steps or operations for presenting one or more training session of the end user application to the end user (Step 812). In accordance with certain aspects of the present disclosure, the training session(s) (Step 812) may be configured to promote and validate one or more cognitive skills in the end user via the presentation of the CSIs in a multitasking format. A performance level of the end user may be measured continuously throughout the training session(s) to determine a measure of time at and/or near the end user's performance threshold for the multitasking CSIs, as determined in the baseline diagnostic session and/or the challenge session. In accordance with certain aspects of the present disclosure, a performance threshold for the end user may be incrementally increased at two or more increments within the training session, as described in more detail in FIG. 9 below. In accordance with certain aspects of the present disclosure, a measure of active therapeutic delivery of the end user application may be correlated to a measure of time at and/or near the end user's performance threshold during the training session of the end user application. In certain embodiments, step 812 may comprise one or more steps or operations for modifying or adjusting one or more graphical elements of the graphical user interface in response to the end user's multitask and/or single task performance being at or near the configured performance threshold for a specified period of time. For example, if the end user's performance is at near the performance threshold (e.g., within a designated percentage) for a specified period of time (e.g., 5 seconds), Step 812 may comprise one or more operations for modifying or adjusting one or more graphical elements of the graphical user interface and/or adding or removing one or more graphical elements within the graphical user interface. For example, in certain embodiment, Step 812 may comprise one or more operations for rendering a portion of the graphical user interface in grayscale; e.g., a portion of the computerized environment. In accordance with certain aspects of the present disclosure, if the end user maintains their task(s) performance at or above the performance threshold for a configured time period (e.g., 7 seconds), Step 812 may comprise one or more operations for rendering one or more graphical elements and/or audio effects at the user interface. In certain embodiments, the one or more graphical elements and/or audio effects are configured as a reward that is indicative of the end user's progress. In accordance with certain aspects of the present disclosure, the performance threshold may be increased in one or more successive increments (e.g., five increments of 20% greater than the previous performance threshold). In certain embodiments, the one or more graphical elements and/or audio effects are indicative that a performance threshold has been reached/satisfied. In an embodiment, the one or more graphical elements may be represented by a star (this is a design choice, and any graphical elements may be readily substituted). In accordance with certain aspects of the present disclosure, routine 800 may comprise one or more steps or operations for determining whether all performance thresholds for a given environment have been satisfied/achieved by the end user (e.g., 5 stars achieved?) (Step 814). If NO, then routine 800 continues to present the CSIs within the training session. If YES, then the training session of the end user application is complete, and the user may proceed to the next computerized environment within the end user application (Step 816).

Figure 9:
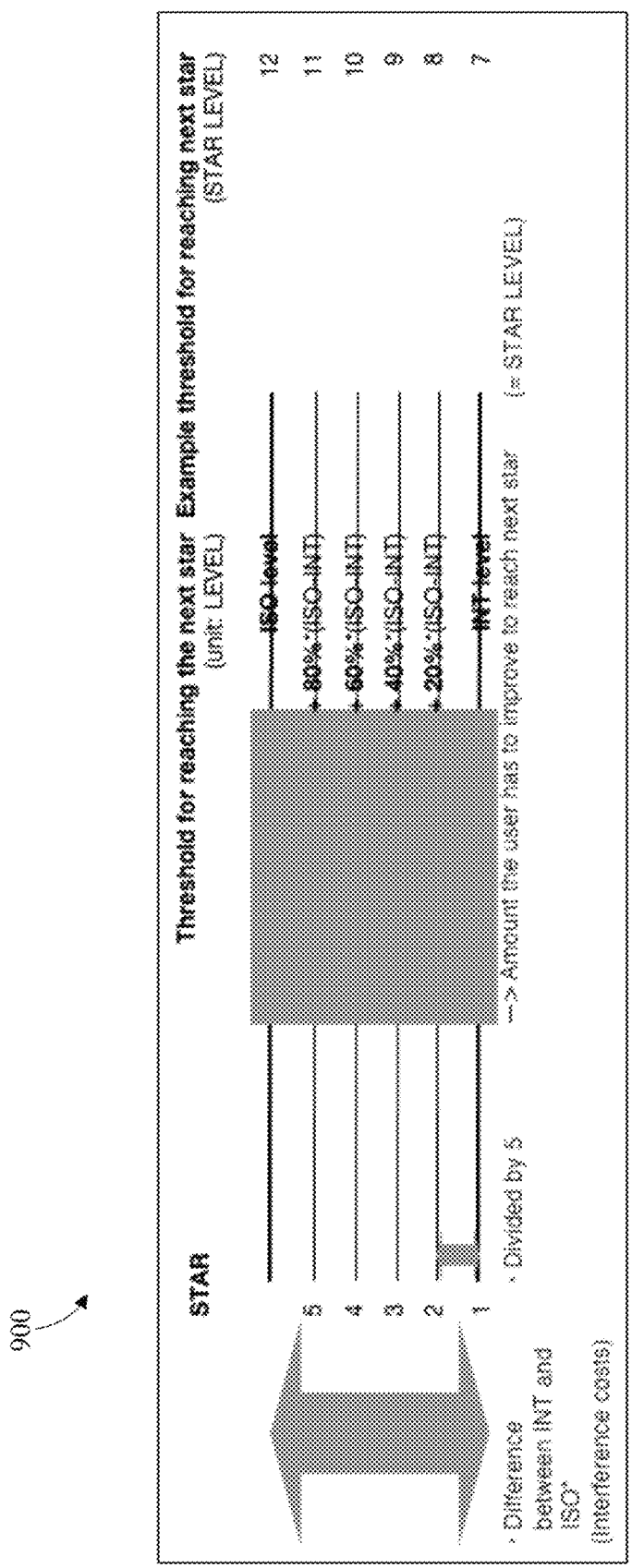
FIG. 9 is a graph of incremental thresholds for algorithmically rendering graphical user interface elements in an SaMD product, in accordance with certain aspects of the present disclosure.

Referring now to FIG. 9, a graph 900 of incremental performance thresholds for algorithmically rendering graphical user interface elements in an SaMD product is shown. In accordance with certain aspects of the present disclosure, as described in FIG. 8 above, an end user may progress through a training session of an end user application based on the end user's incremental improvement in performing one or more computerized tasks; e.g., a targeting task and a navigation task. As shown in FIG. 9, the end user's "ISO" level may represent the end user's baseline performance measure for performing one of the computerized tasks in isolation; e.g., performing the targeting task or the navigation task in isolation. The end user's "INT" level may represent the end user's baseline performance measure for performing both of the computerized tasks in a multitasking format; e.g., performing the targeting task and the navigation task concurrently or concomitantly. The INT level may comprise the end user's initial performance threshold. In accordance with certain aspects of the present disclosure, as shown in FIG. 9, a "threshold for reaching the next star level" represents a predetermined incremental improvement (e.g., 20%) in the difference between the end user's ISO level and INT level. More particularly, as the user's INT level approaches the user's ISO level, the user is measured as progressing or improving within the training session of the end user application. In accordance with certain embodiments, as the user approaches each performance threshold, the end user application may be configured to modify, adjust and/or present one or more graphical user interface elements for a specified amount of time (e.g., render a portion of the user interface in grayscale). In certain embodiments, the end user application may present one or more graphical elements (e.g., a star, an orb, a character, or other reward) in response to the user achieving/satisfying a performance threshold. In accordance with certain embodiments, as the user achieves a performance threshold, the end user application is configured to increase the performance threshold to the next increment. In accordance with certain embodiments, the basis for the "Star Level," as shown in FIG. 9, is the difference between the INT and ISO scores calculated during the challenge session of the end user application and/or the baseline diagnostic session (as discussed in FIG. 8). In accordance with certain embodiments, the end user application may be configured to present a first graphical element to the end user (e.g., "first star") in response to determining that the end user is performing at their INT threshold within the training session. The end user application may be configured wherein the end user must improve by 20% based on the difference between ISO and INT levels to earn the next reward (e.g., "star"). In certain embodiments, a final threshold is satisfied when the user's INT level reaches 80% of their ISO level.

Figure 10:
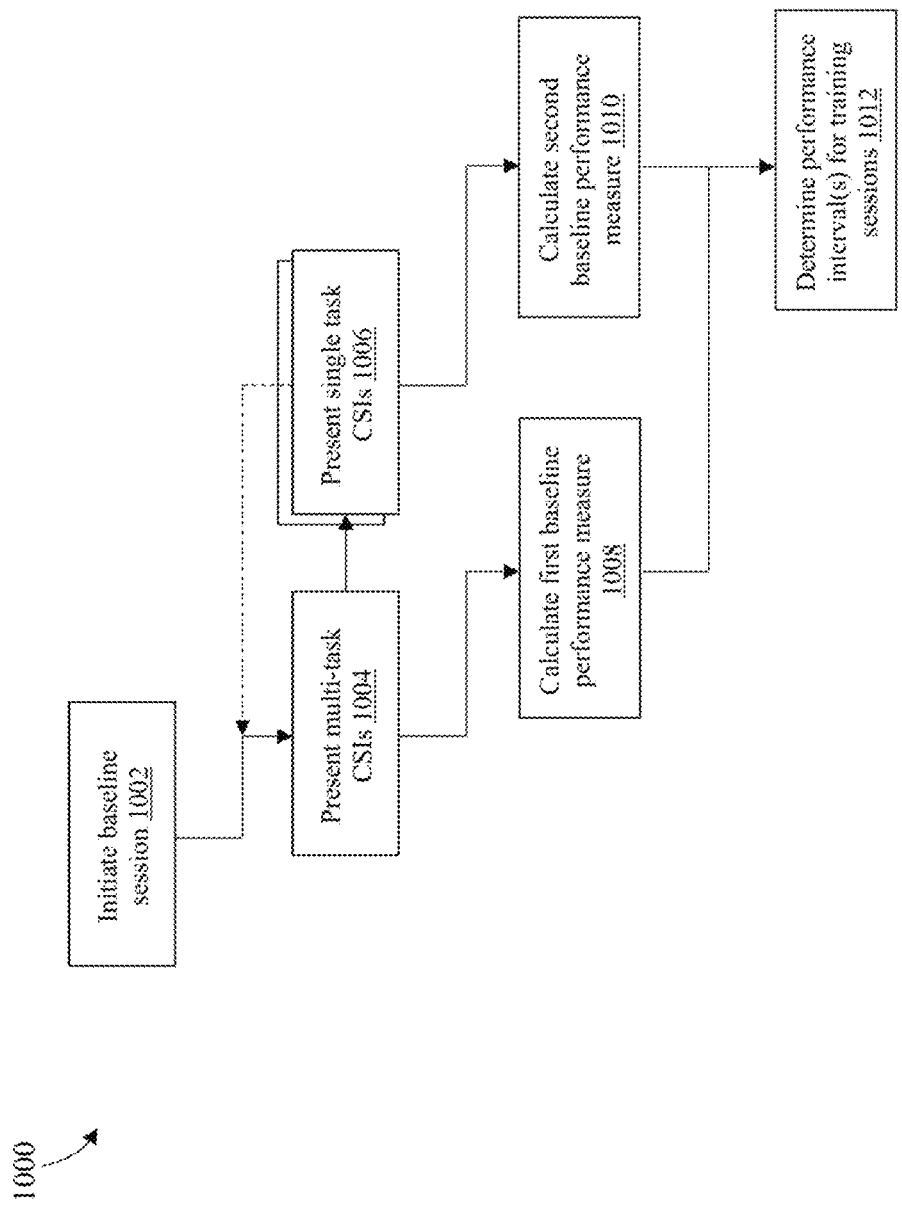
FIG. 10 is a process flow diagram of a method and system for algorithmically rendering graphical user interface elements in an SaMD product, in accordance with certain aspects of the present disclosure.

Referring now to FIG. 10, a process flow diagram of a routine 1000 of a method and system for algorithmically rendering graphical user interface elements in an SaMD product is shown. In accordance with certain aspects of the present disclosure, routine 1000 may be embodied within one or more of graphical user interfaces 202*a-e*, as shown in FIGS. 2-6; and/or may be embodied within method 700, as shown in FIG. 7; and/or may incorporate one or more steps or operations for routine 800, as shown in FIG. 8. In accordance with certain aspects of the present disclosure, routine 1000 may comprise one or more steps or operations for initiating a baseline session within an end user instance of a computerized cognitive training application (Step 1002). Step 1002 may comprise one or more steps or operations for presenting one or more CSIs associated with at least a first computerized task (e.g., a targeting task) and a second computerized task (e.g., a navigation task). Routine 1000 may proceed by executing one or more steps or operations for presenting (e.g., within a graphical user interface of the computerized cognitive training application) the one or more CSIs in a multitasking format (Step 1004) and presenting the or more CSIs in a single task format. In accordance with certain embodiments, routine 1000 may comprise one or more steps or operations for presenting the one or more CSIs in an initial multitasking phase, a first task in isolation phase, a second task in isolation phase, and a final multitasking phase. Routine 1000 may proceed by executing one or more steps or operations for calculating a first baseline performance measure based on the user-generated inputs received during the multitasking phase(s) (Step 1008). Routine 1000 may proceed, concurrently or sequentially, by executing one or more steps or operations for calculating a second baseline performance measure based on the user-generated inputs received during the single tasking phase(s) (Step 1010). In accordance with certain aspects of the present disclosure, an output of Step 1008 may comprise calculating an initial performance threshold for the end user for multitasking and an output of Step 1010 may comprise calculating an initial performance threshold for the end user for single tasking. In certain embodiments, an output of Step 1008 and/or Step 1010 may comprise calculating an interference cost of one or more distractors or interrupters presented during a multitasking phase. In accordance with certain aspects of the present disclosure, routine 1000 may proceed by performing one or more steps or operations for determining one or more performance intervals for the end user for use during one or more training sessions of the computerized cognitive training application (Step 1012).

Figure 11:
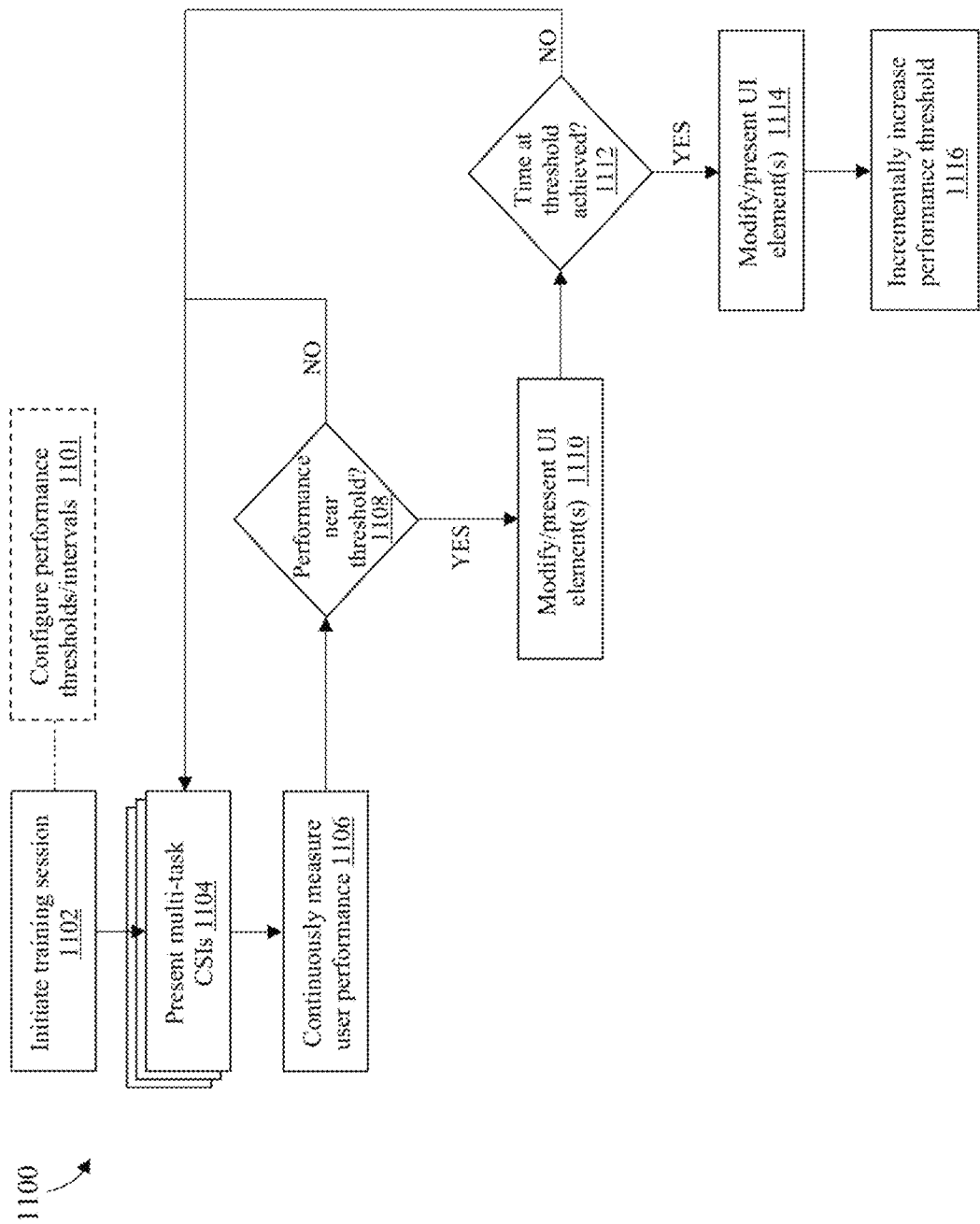
FIG. 11 is a process flow diagram of a method and system for algorithmically rendering graphical user interface elements in an SaMD product, in accordance with certain aspects of the present disclosure.

Referring now to FIG. 11, a routine 1100 of a method and system for algorithmically rendering graphical user interface elements in an SaMD product is shown. In accordance with certain aspects of the present disclosure, routine 1100 may be successive or sequential to one or more steps of routine 1000, as shown in FIG. 10. Routine 1100 may be embodied within one or more of graphical user interfaces 202*a-e*, as shown in FIGS. 2-6; and/or may be embodied within method 700, as shown in FIG. 7; and/or may incorporate one or more steps or operations of routine 800, as shown in FIG. 8. In accordance with certain aspects of the present disclosure, routine 1100 may comprise one or more steps or operations for initiating a training session of a computerized cognitive training application at a display of an end user device (Step 1102). Step 1102 may comprise one or more steps or sub steps for configuring one or more performance threshold and/or performance intervals for use in the training session (Step 1101). In accordance with certain aspects of the present disclosure, Step 1101 may comprise an output of routine 1000, as shown in FIG. 10. Routine 1100 may proceed by executing one or more steps or operations for presenting one or more CSIs in a multitasking format during the instance of the training session (Step 1104). Routine 1100 may proceed by executing one or more steps or operations for continuously measuring user performance according to a plurality of user-generated inputs submitted in response to the one or more CSIs (Step 1106). Routine 1100 may proceed by executing one or more steps or operations for determining (e.g., based on an output from Step 1106) whether the user's performance is at or near a configured performance threshold (Step 1108). In accordance with certain embodiments, Step 1108 may comprise one or more steps or operations for determining whether the user's performance is at or near a configured performance threshold for a specified time interval (e.g., 5 seconds). If an output from Step 1108 is NO, then routine 1100 continues to present the multitasking CSIs within the instance of the training session. If an output from Step 1108 is YES, then routine 1100 proceeds by modifying and/or presenting one or more graphical elements at the graphical user interface (Step 1110). In certain embodiments, Step 1110 comprises one or more steps or operations for rendering a portion of the graphical user interface in grayscale while maintaining a sub-portion of the graphical user interface in color. In certain embodiments, Step 1110 is configured to promote an emotional threshold or gradient for the end user. Step 1110 may comprise modifying or presenting one or more user interface elements including, but not limited to, one or more computerized adjustable element (e.g., scale, scorecard, or meter), speed of a vehicle/avatar, selection of music, volume of audio, one or more sounds, one or more camera views (e.g., zoom and/or angle) and the like.

In accordance with certain aspects of the present disclosure, routine 1100 may proceed by performing one or more steps or operations for determining whether the user has satisfied a specified time at the performance threshold (Step 1112). If NO, then routine 1100 proceeds back to Step 1104. If YES, then routine 1100 may execute one or more steps or operations to modify and/or present one or more user interface elements at the graphical user interface (Step 1114). In certain embodiments, Step 1114 may comprise restoring one or more user interface elements to a previous state. For example, in embodiments where Step 1110 is configured to render a portion of the graphical user interface in grayscale, Step 1114 may comprise one or more steps or operations to restore a color setting of the graphical user interface to a previous state. In certain embodiments, Step 1114 may comprise one or more steps or operations for modifying a computerized adjustable element and/or presenting a graphical element to indicate that the user has achieved an incremental performance level. In accordance with certain aspects of the present disclosure, routine 1100 may comprise one or more steps or operations for incrementally increasing the performance threshold within the training session of the computerized cognitive training application (Step 1116).

Figure 12:
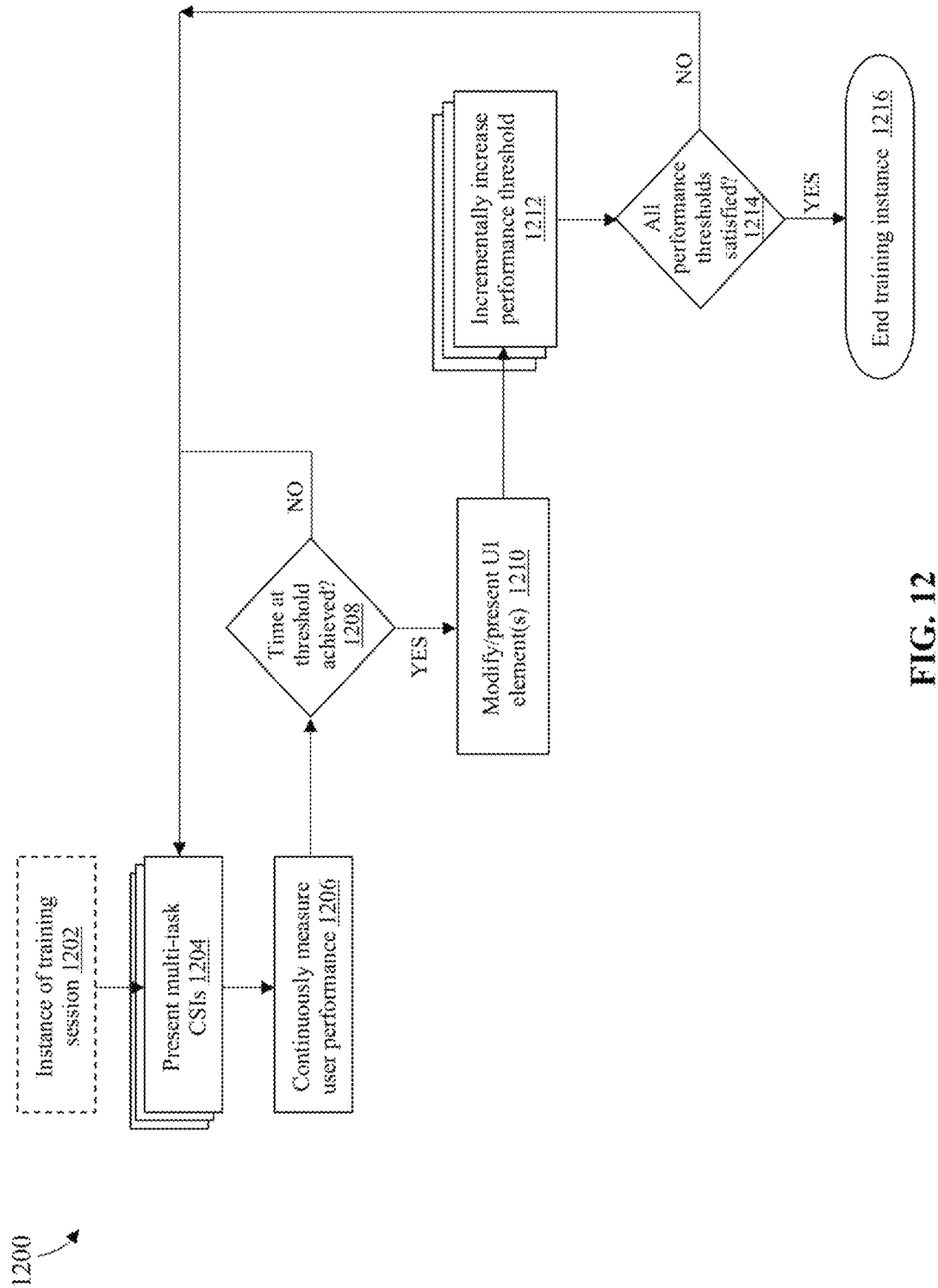
FIG. 12 is a process flow diagram of a method and system for algorithmically rendering graphical user interface elements in an SaMD product, in accordance with certain aspects of the present disclosure.

Referring now to FIG. 12, a process flow diagram of a routine 1200 of a method and system for algorithmically rendering graphical user interface elements in an SaMD product is shown. In accordance with certain aspects of the present disclosure, routine 1200 may be successive or sequential to one or more steps of routine 1000, as shown in FIG. 10. Routine 1200 may be successive or sequential to one or more steps of routine 1100, as shown in FIG. 11, and may comprise one or more sub steps of routine 1100. Routine 1200 may be embodied within one or more of graphical user interfaces 202*a*-*e*, as shown in FIGS. 2-6; and/or may be embodied within method 700, as shown in FIG. 7; and/or may incorporate one or more steps or operations of routine 800, as shown in FIG. 8.

In accordance with certain aspects of the present disclosure, routine 1200 may comprise one or more operations for executing an instance of a training session of a computerized cognitive training application (Step 1202). Routine 1200 may comprise one or more steps or operations for presenting one or more multitasking CSIs to an end user within the instance of the training session (Step 1204). Routine 1200 may comprise one or more steps or operations for continuously measuring user performance for the one or more multitasking CSIs by receiving and processing a plurality of user-generated inputs received at a user interface (e.g., user device) in response to the one or more multitasking prompts (Step 1206). Routine 1200 may comprise one or more steps or operations for determining whether a time at or near a current performance threshold for the instance of the computerized cognitive training application has been achieved (Step 1208). Step 1208 may be based on one or more outputs of Step 1206. If the output of Step 1208 is NO, then routine 1200 proceeds to Step 1204. If the output of Step 1208 is YES, then routine 1200 proceeds to execute one or more steps or operations to modify, render, adjust and/or present one or more user interface elements to the end user via the graphical user interface of the computerized cognitive training application (Step 1210). Step 1210 may comprise one or more steps or operations for adjusting one or more aspects of a computerized environment (e.g., rendering a portion of the computerized environment in grayscale) and/or may comprise one or more steps or operations for presenting a new/different computerized environment within the training instance of the computerized cognitive training application. Routine 1200 may comprise one or more steps or operations for incrementally increasing the performance threshold for the user within the training instance of the computerized cognitive training application (Step 1212). In certain embodiments, Step 1212 may comprise one or more steps or operations for incrementally increasing the performance threshold for the user within the training instance of the computerized cognitive training application as described in FIG. 9. Routine 1200 may proceed by executing one or more steps or operations for determining whether all of the performance thresholds for the training instance of the computerized cognitive training application have been satisfied (Step 1214). If NO, then the training instance continues by routine 1200 proceeding to step 1204. If YES, then routine 1200 concludes by ending the training instance of the computerized cognitive training application (Step 1216).

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

Any suitable transitory or non-transitory computer readable medium may be utilized. The computer readable medium may be, for example but not limited to, an electronic, magnetic, optical, electromagnetic, infrared, or semiconductor system, apparatus, or device. More specific examples of the computer readable medium include, but are not limited to, the following: an electrical connection having one or more wires; a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device.

In the context of this document, a computer readable medium may be any medium that can contain, store, communicate, or transport the program for use by or in connection with the instruction execution system, apparatus, or device. The computer usable program code may be transmitted using any appropriate medium, including but not limited to the Internet, wireline, optical fiber cable, radio frequency (RF) signals, or other mediums.

Computer-executable program code for carrying out operations of embodiments of the present invention may be written in an object oriented, scripted or unscripted programming language such as Java, Perl, Smalltalk, C++, or the like. However, the computer program code for carrying out operations of embodiments of the present invention may also be written in conventional procedural programming languages, such as the "C" programming language or similar programming languages.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general-purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

These computer-executable program code portions (i.e., computer-executable instructions) may also be stored in a computer-readable memory that can direct a computer or other programmable data processing apparatus to function in a particular manner, such that the code portions stored in the computer readable memory produce an article of manufacture including instruction mechanisms which implement the function/act specified in the flowchart and/or block diagram block(s). Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as predetermined in various embodiments.

The computer-executable program code may also be loaded onto a computer or other programmable data processing apparatus to cause a series of operational phases to be performed on the computer or other programmable apparatus to produce a computer-implemented process such that the code portions which execute on the computer or other programmable apparatus provide phases for implementing the functions/acts specified in the flowchart and/or block diagram block(s). Alternatively, computer program implemented phases or acts may be combined with operator or human implemented phases or acts in order to carry out an embodiment of the invention.

As the phrases are used herein, a processor may be "operable to" or "configured to" perform a certain function in a variety of ways, including, for example, by having one or more general-purpose circuits perform the function by executing particular computer-executable program code embodied in computer-readable medium, and/or by having one or more application-specific circuits perform the function.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." As used herein, the terms "right," "left," "top," "bottom," "upper," "lower," "inner" and "outer" designate directions in the drawings to which reference is made.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The present disclosure includes that contained in the appended claims as well as that of the foregoing description. Although this invention has been described in its exemplary forms with a certain degree of particularity, it is understood that the present disclosure of has been made only by way of example and numerous changes in the details of construction and combination and arrangement of parts may be employed without departing from the spirit and scope of the invention.

What is claimed is:

1. A computer-implemented method for modifying a graphical user interface at an end user device, the computer-implemented method comprising:
   presenting, with at least one processor, an instance of an end user application to an end user, the end user application comprising the graphical user interface at a display of the end user device, wherein the end user application comprises one or more computerized stimuli or interactions comprising at least one computerized task;
   receiving, with at least one input device of the end user device, a plurality of user-generated responses in response to the one or more computerized stimuli or interactions;
   determining, with the at least one processor, at least one performance measure for the end user based on the plurality of user-generated responses; and
   modifying, with the at least one processor, one or more graphical elements of the graphical user interface in response to determining the at least one performance measure for the end user based on the plurality of user-generated responses,
   wherein modifying the one or more graphical elements comprises rendering a portion of the graphical user interface in grayscale while maintaining a sub-portion of the graphical user interface in color,
   wherein the sub-portion of the graphical user interface comprises one or more therapeutically active elements associated with the at least one computerized task,
   wherein the portion of the graphical user interface rendered in grayscale comprises one or more therapeutically inactive elements or ornamental elements associated with the at least one computerized task.

2. The computer-implemented method of claim 1 wherein modifying the one or more graphical elements comprises adding or removing one or more graphical elements within the graphical user interface.

3. The computer-implemented method of claim 2 wherein modifying the one or more graphical elements comprises adding or modifying at least one graphical element configured to indicate that the end user has achieved the at least one performance measure.

4. The computer-implemented method of claim 1 further comprising restoring, with the at least one processor, the graphical user interface to a state prior to modifying the one or more graphical elements.

5. The computer-implemented method of claim 4 further comprising incrementally increasing the at least one performance measure in response to restoring the graphical user interface to a state prior to modifying the one or more graphical elements.

6. The computer-implemented method of claim 4 wherein restoring the graphical user interface to the state prior to modifying the one or more graphical elements comprising restoring a color setting of the graphical user interface.

7. The computer-implemented method of claim 1 wherein the end user application comprises a computerized cognitive treatment application.

8. The computer-implemented method of claim 7 wherein the at least one performance measure correlates to a threshold of active therapeutic delivery for the end user within the instance of the end user application.

9. The computer-implemented method of claim 8 wherein the one or more computerized stimuli or interactions comprise at least two computerized tasks.

10. The computer-implemented method of claim 1 further comprising analyzing, with the at least one processor, the plurality of user-generated responses according to a predetermined stimulus-response framework or algorithm.

11. A computer-implemented system comprising:
    an end user device comprising a display and at least one input device;
    a processor operably engaged with the end user device to render a graphical user interface of an end user application at the display; and
    a non-transitory computer readable medium operably engaged with the processor, the non-transitory computer-readable medium comprising one or more processor-executable instructions stored thereon that, when executed, command the processor to perform one or more operations, the one or more operations comprising:
    presenting an instance of an end user application to an end user, the end user application comprising the graphical user interface at a display of the end user device, wherein the end user application comprises one or more computerized stimuli or interactions comprising at least one computerized task;
    receiving, via the at least one input device, a plurality of user-generated responses in response to the one or more computerized stimuli or interactions;

determining at least one performance measure for the end user based on the plurality of user-generated responses; and modifying one or more graphical elements of the graphical user interface in response to determining the at least one performance measure for the end user based on the plurality of user-generated responses, wherein modifying the one or more graphical elements comprises rendering a portion of the graphical user interface in grayscale while maintaining a sub-portion of the graphical user interface in color, wherein the sub-portion of the graphical user interface comprises one or more therapeutically active elements associated with the at least one computerized task, wherein the portion of the graphical user interface rendered in grayscale comprises one or more therapeutically inactive elements or ornamental elements associated with the at least one computerized task.

12. The computer-implemented system of claim 11 wherein modifying the one or more graphical elements comprises adding or removing one or more graphical elements within the graphical user interface.

13. The computer-implemented system of claim 12 wherein modifying the one or more graphical elements comprises adding or modifying at least one graphical element configured to indicate that the end user has achieved the at least one performance measure.

14. The computer-implemented system of claim 13 wherein the one or more operations further comprise analyzing, with the at least one processor, the plurality of user-generated responses according to a predetermined stimulus-response framework or algorithm.

15. The computer-implemented system of claim 11 wherein the end user application comprises a computerized cognitive treatment application.

16. The computer-implemented system of claim 15 wherein the at least one performance measure correlates to a threshold of active therapeutic delivery to the end user within the instance of the end user application.

17. The computer-implemented system of claim 11 wherein the one or more operations further comprise restoring the graphical user interface to a state prior to modifying the one or more graphical elements.

18. The computer-implemented system of claim 17 wherein restoring the graphical user interface to the state prior to modifying the one or more graphical elements comprising restoring a color setting of the graphical user interface.

19. The computer-implemented system of claim 17 wherein the one or more operations further comprise incrementally increasing the at least one performance measure in response to restoring the graphical user interface to a state prior to modifying the one or more graphical elements.

20. A non-transitory computer-readable medium with one or more processor-executable instructions stored thereon that, when executed, command one or more processors to perform one or more operations, the one or more operations comprising:

presenting an instance of an end user application to an end user, the end user application comprising the graphical user interface at a display of the end user device, wherein the end user application comprises one or more computerized stimuli or interactions comprising at least one computerized task;

receiving a plurality of user-generated responses in response to the one or more computerized stimuli or interactions;

determining at least one performance measure for the end user based on the plurality of user-generated responses; and modifying one or more graphical elements of the graphical user interface in response to determining the at least one performance measure for the end user based on the plurality of user-generated responses, wherein modifying the one or more graphical elements comprises rendering a portion of the graphical user interface in grayscale while maintaining a sub-portion of the graphical user interface in color, wherein the sub-portion of the graphical user interface comprises one or more therapeutically active elements associated with the at least one computerized task, wherein the portion of the graphical user interface rendered in grayscale comprises one or more therapeutically inactive elements or ornamental elements associated with the at least one computerized task.

* * * * *